US012611127B2

(12) United States Patent
Shin et al.

(10) Patent No.: US 12,611,127 B2
(45) Date of Patent: Apr. 28, 2026

(54) DIAGNOSIS DEVICE USING SALIVA AND DIAGNOSIS METHOD USING THE SAME

(71) Applicant: DONGWOON ANATECH CO., LTD., Seoul (KR)

(72) Inventors: Ik Soo Shin, Seoul (KR); Hee Jae Woo, Seoul (KR); In Su Jang, Seoul (KR); Dong Cheol Kim, Seoul (KR)

(73) Assignee: DONGWOON ANATECH CO., LTD., Seoul (KR)

( * ) Notice: Subject to any disclaimer, the term of this patent is extended or adjusted under 35 U.S.C. 154(b) by 0 days.

(21) Appl. No.: 15/766,270

(22) PCT Filed: Nov. 24, 2017

(86) PCT No.: PCT/KR2017/013487
§ 371 (c)(1),
(2) Date: Apr. 5, 2018

(87) PCT Pub. No.: WO2018/117448
PCT Pub. Date: Jun. 28, 2018

(65) Prior Publication Data
US 2019/0298233 A1 Oct. 3, 2019

(30) Foreign Application Priority Data

Dec. 21, 2016 (KR) ........................ 10-2016-0175951
Jan. 31, 2017 (KR) ........................ 10-2017-0013783

(51) Int. Cl.
*A61B 5/1486* (2006.01)
*A61B 5/145* (2006.01)
(Continued)

(52) U.S. Cl.
CPC ........ *A61B 5/1486* (2013.01); *A61B 5/14507* (2013.01); *A61B 5/14532* (2013.01);
(Continued)

(58) Field of Classification Search
CPC ............ A61B 5/14532; A61B 5/02438; A61B 5/14507; A61B 5/14546; A61B 10/0051;
(Continued)

(56) References Cited

U.S. PATENT DOCUMENTS 6,558,321 B1 * 5/2003 Burd ...................... C12Q 1/006
600/300
7,198,708 B2 4/2007 Atkinson et al.
(Continued)

FOREIGN PATENT DOCUMENTS

CN 1300025 A 6/2001
CN 1675539 A 9/2005
(Continued)

OTHER PUBLICATIONS

B. Kong , C. Selomulya , G. Zheng and D. Zhao , New faces of porous Prussian blue: interfacial assembly of integrated hetero-structures for sensing applications, Chem. Soc. Rev., 2015, 44 , 7997-8018 (Year: 2015).*
(Continued)

*Primary Examiner* — Tse W Chen
*Assistant Examiner* — Michael A Catina
(74) *Attorney, Agent, or Firm* — Foley & Lardner LLP

(57) ABSTRACT

Disclosed are a diagnosis device using saliva and a diagnosis method using the same. According to the present invention, it is possible to diagnose diseases by using saliva instead of blood and to utilize (measure) saliva for each particular purpose (disease) by allowing a detection unit suitable for a particular purpose (disease) to react with saliva, there may be an economic advantage in that it is possible to diagnose diseases several times even in a day without causing pain by using saliva and to select and use the detection unit for measurement for each particular purpose (disease), and a measurement result may be provided to a user terminal, such (Continued)

that a user may manage his/her health based on the measurement result and individually carry out self-health care.

28 Claims, 9 Drawing Sheets

(51) Int. Cl.

| | |
|---|---|
| *A61B 10/00* | (2006.01) |
| *G01N 27/04* | (2006.01) |
| *G01N 27/327* | (2006.01) |
| *G01N 33/48* | (2006.01) |
| *G01N 33/50* | (2006.01) |
| *G06Q 50/22* | (2018.01) |
| *A61B 5/1468* | (2006.01) |

(52) U.S. Cl.
CPC .......... *A61B 10/0051* (2013.01); *G01N 27/04* (2013.01); *G01N 27/3272* (2013.01); *G01N 33/48* (2013.01); *G01N 33/50* (2013.01); *G06Q 50/22* (2013.01); *A61B 5/14546* (2013.01); *A61B 5/1468* (2013.01)

(58) Field of Classification Search
CPC ..... A61B 5/682; A61B 5/4277; A61B 5/4836; A61B 5/4839
See application file for complete search history.

(56) References Cited

U.S. PATENT DOCUMENTS

| | | | |
|---|---|---|---|
| 9,244,035 B2 | 1/2016 | Zhang et al. | |
| 11,980,462 B2 | 5/2024 | Wang et al. | |
| 2001/0023324 A1* | 9/2001 | Pronovost .......... | A61B 5/14532 600/365 |
| 2005/0176136 A1* | 8/2005 | Burd .................... | A61B 5/6801 600/315 |
| 2006/0081469 A1 | 4/2006 | Lee | |
| 2007/0197890 A1* | 8/2007 | Boock ................ | A61B 5/14865 600/365 |
| 2008/0026473 A1* | 1/2008 | Wang .................... | C12Q 1/006 436/63 |
| 2009/0188791 A1 | 7/2009 | Neubert et al. | |
| 2013/0197332 A1* | 8/2013 | Lucisano ........... | A61B 5/14542 600/345 |
| 2014/0046600 A1 | 2/2014 | Avner | |
| 2014/0259652 A1* | 9/2014 | Pushpala .......... | A61B 5/150984 29/825 |
| 2016/0097734 A1 | 4/2016 | Zhang et al. | |
| 2017/0014822 A1 | 1/2017 | Ker | |

FOREIGN PATENT DOCUMENTS

| | | | |
|---|---|---|---|
| CN | 102323310 A | | 1/2012 |
| CN | 105102972 A | | 11/2015 |
| JP | H09201337 | | 8/1997 |
| JP | 2000-074914 | A | 3/2000 |
| JP | 2002-122562 | A | 4/2002 |
| JP | 2006-075447 | A | 3/2006 |
| JP | 2007-142835 | A | 6/2007 |
| JP | 2010-025728 | A | 2/2010 |
| KR | 101323373 | B1 | 10/2013 |
| KR | 20160017684 | | 2/2016 |
| KR | 20160017684 | A | 2/2016 |
| KR | 20160111399 | | 9/2016 |
| KR | 20160111399 | A | 9/2016 |
| WO | WO-02/18924 | A1 | 3/2002 |
| WO | 2015112638 | | 7/2015 |
| WO | WO-2015/112638 | A1 | 7/2015 |

OTHER PUBLICATIONS

International Search Report and Written Opinion of International Application No. PCT/KR2017/013487 mailed Mar. 13, 2018.
Jang, S.C. et al., "Adsorption Mechanism of Radioactive Cesium by Prussian Blue", Journal of Radiation Industry, 2015, vol. 9(3), pp. 127-130, (Abstract only).
Extended European Search Report issued in connection with EP Appl. No. 17861188.5 dated Aug. 31, 2020.
Extended European Search Report issued in connection with EP Appl. No. 23182929.2 dated Jul. 14, 2023.
Extended European Search Report issued in connection with EP Appl. No. 23182930.0 dated Jul. 14, 2023.
Kong, B. et al., New faces of porous Prussian blue: interfacial assembly of integrated hetero-structures for sensing, Chemical Society Reviews, vol. 44, , 2015 . . . , , p. 7997-8018.
Li Jinging et al., "Study on Mobile Phone Enabled Wireless Detection of Saliva Glucose", Chinese Medical Journal of Medical Devices, vol. 35, Issue 5, pp. 317-323.
Office Action issued in connection with Chinese Appl. No. 201780003592.4 dated Apr. 15, 2020.
Office Action issued in connection with Chinese Appl. No. 201780003592.4 dated Aug. 5, 2019.
Office Action issued in connection with Chinese Appl. No. 201780003592.4 dated Jan. 16, 2020.
Office Action issued in connection with Indian Appl. No. 201837047422 dated Apr. 9, 2021.
Office Action issued in connection with Japanese Appl. No. 2018-514435 dated Jan. 21, 2019.
Office Action issued in connection with Korean Appl. No. 10-2017-0013783 dated Apr. 19, 2018.
Wang Chun-lei et al., "Microporous Prussian Blue/gold composite material based enzyme eletrochemical sensor", Shangdong Science, vol. 28 issue 2, p. 53-57.
H. J. Buser et al., "The Crystal Structure of Prussian Blue", Inorganic Chemistry, vol. 16/Issue 11, 1977.
Zhu et al., "Planar Amperometric Glucose Sensor Based on Glucose Oxidase Immobilized by Chitosan Film on Prussian Blue Layer", Sensors, 2002, 10 pages.

* cited by examiner

ELECTRONIC
DEVICE

SALIVA SAMPLE ~105

STRIP
ELECTRODE UNIT

ACTIVE LAYER = GLUCOSE OXIDASE +
ORGANIC MATTER SUPPORT +
NONTOXIC NANO-CATALYST STRUCTURE

160

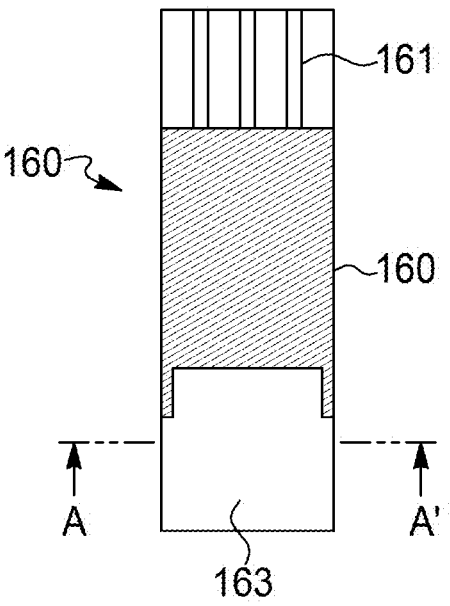
FIG. 5A
L5
L4
L3
L2
L1
FIG. 5B
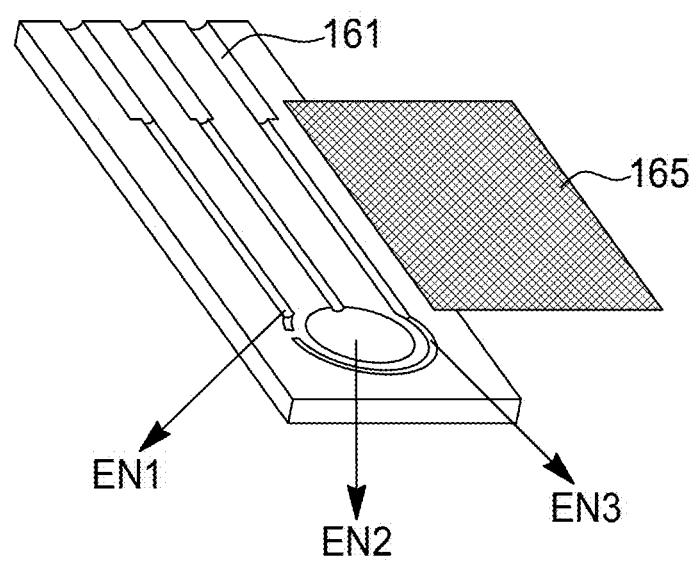
FIG. 6

CHANGE IN ELECTRIC CURRENT SIGNAL IN ACCORDANCE
WITH GLUCOSE CONCENTRATION OF 1 to 2400 μM

FIG. 10A

DIAGNOSIS DEVICE USING SALIVA AND DIAGNOSIS METHOD USING THE SAME

TECHNICAL FIELD

The present invention relates to a diagnosis device using saliva and a diagnosis method using the same, and more particularly, to a device and a method for diagnosing a disease by using saliva.

BACKGROUND ART

All existing bio sensors for diagnosing diseases are, in terms of an operational principle, diagnosis instruments employing invasive blood drawing methods, that is, separate diagnosis instruments configured to diagnose diseases by drawing blood and used only for one purpose such as the purpose of measuring blood glucose of a diabetic patient or the purpose of measuring cancer.

DISCLOSURE

Technical Problem

A technical problem to be solved by the present invention is to provide a diagnosis device using saliva, which is capable of diagnosing diseases by using saliva instead of blood and capable of utilizing (measuring) saliva for each particular purpose (disease) by allowing a detection unit suitable for a particular purpose (disease) to react with saliva, and a diagnosis method using the same.

Technical Solution

To solve the aforementioned technical problem, a diagnosis device using saliva according to the present invention includes: a detection unit which is detachably coupled to the diagnosis device and diagnoses a disease by using saliva; a communication unit; and a control unit which applies voltage to the detection unit, converts diagnosis data, which are provided through the detection unit, into a digital signal, and provides the digital signal to a user terminal through the communication unit.

The detection unit may induce an electrochemical reaction of a disease factor in the saliva by the voltage applied through the diagnosis device, and may provide the control unit with electric current generated by the electrochemical reaction of the disease factor.

The detection unit may include: a device connecting unit which is supplied with the voltage from the diagnosis device, and provides the diagnosis device with the electric current generated by the electrochemical reaction of the disease factor in the saliva; and a saliva detecting unit which induces the electrochemical reaction of the disease factor in the saliva by the voltage applied from the diagnosis device through the device connecting unit, and provides the device connecting unit with the electric current generated by the electrochemical reaction of the disease factor.

The saliva detecting unit may include: a first layer which is configured as an electrode connected to the device connecting unit; a second layer which is attached to the first layer and induces the electrochemical reaction of the disease factor in the saliva; a third layer which is positioned on the second layer and includes an enzyme that detects the disease factor in the saliva; a fourth layer which is positioned on the third layer and configured as a filter for separating a predetermined material; and a fifth layer which is positioned on the fourth layer and formed by a composite fiber membrane.

The disease factor may be a particular factor capable of diagnosing a disease.

The second layer may have a nanostructure formed in the form of a porous metal-organic solid structure.

The nanostructure may have a chemical composition, $M_a(II)M'_b(III)(CN)_6$, and M and M' may be metal elements.

The digital signal may be converted into concentration of the disease factor by the user terminal based on a predetermined calibration curve.

To solve the aforementioned technical problem, a diagnosis method using a diagnosis device using saliva according to the present invention includes: applying voltage to a detection unit detachably coupled to the diagnosis device; diagnosing a disease by using saliva by the detection unit; converting diagnosis data, which are provided through the detection unit, into a digital signal; and providing the digital signal to a user terminal via a communication network.

The diagnosing of the disease may include: inducing an electrochemical reaction of a disease factor in the saliva by the voltage applied to the detection unit through the diagnosis device; and detecting electric current generated by the electrochemical reaction of the disease factor.

The detection unit may include: a device connecting unit which is supplied with the voltage from the diagnosis device, and provides the diagnosis device with the electric current generated by the electrochemical reaction of the disease factor in the saliva; and a saliva detecting unit which induces the electrochemical reaction of the disease factor in the saliva by the voltage applied from the diagnosis device through the device connecting unit, and provides the device connecting unit with the electric current generated by the electrochemical reaction of the disease factor.

The saliva detecting unit may include: a first layer which is configured as an electrode connected to the device connecting unit; a second layer which is attached to the first layer and induces the electrochemical reaction of the disease factor in the saliva; a third layer which is positioned on the second layer and includes an enzyme that detects the disease factor in the saliva; a fourth layer which is positioned on the third layer and configured as a filter for separating a predetermined material; and a fifth layer which is positioned on the fourth layer and formed by a composite fiber membrane.

The disease factor may be a particular factor capable of diagnosing a disease.

The second layer may have a nanostructure formed in the form of a porous metal-organic solid structure.

The nanostructure may have a chemical composition, $M_a(II)M'_b(III)(CN)_6$, and M and M' may be metal elements.

The digital signal may be converted into concentration of the disease factor by the user terminal based on a predetermined calibration curve.

To solve the aforementioned technical problem, a computer program according to the present invention is stored in a computer-readable recording medium and performs, on a computer, any one of the aforementioned methods.

Advantageous Effects

According to the diagnosis device using saliva and the diagnosis method using the same according to the present invention, it is possible to diagnose diseases several times even in a day without causing pain by using saliva instead of blood. In addition, there may be an economic advantage in that the detection unit may be selected and used for measurement for each particular purpose (disease). More-over, a measurement result is provided to a user terminal via a communication network, and as a result, a user may manage his/her health based on the measurement result, and thus may individually carry out self-health care.

DESCRIPTION OF DRAWINGS

FIG. 5A is a view for explaining an example of the detection unit illustrated in FIG. 3, and FIG. 5B is a cross-sectional view taken along line A-A' illustrated in FIG. 5A.

FIG. 6 is a view for explaining a state in which a protective cover unit is separated from the detection unit illustrated in FIG. 5.

MODES OF THE INVENTION

Hereinafter, exemplary embodiments of a diagnosis device using saliva and a diagnosis method using the same according to the present invention will be described in detail with reference to the accompanying drawings.

First, a diagnosis device using saliva according to an exemplary embodiment of the present invention will be described with reference to FIGS. 1 and 2.

Figures 1, 2:
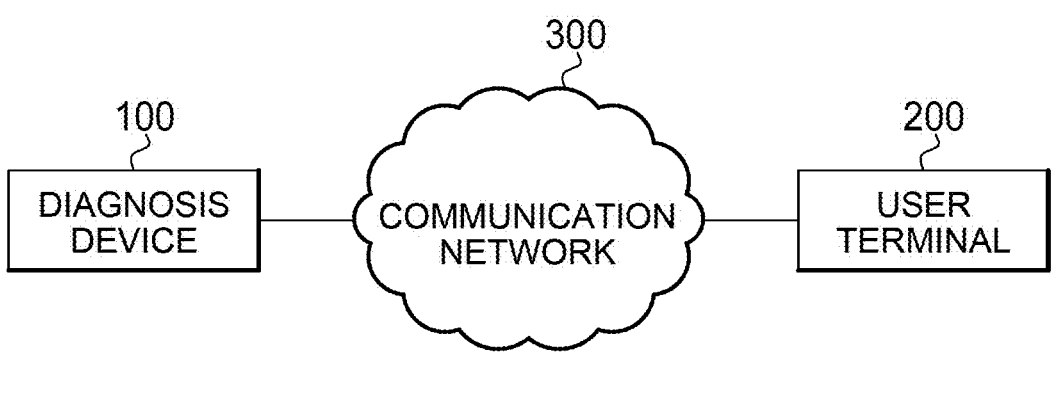
FIG. 1 is a block diagram for explaining a diagnosis device using saliva according to an exemplary embodiment of the present invention.
FIG. 2 is a view for explaining an example of the diagnosis device illustrated in FIG. 1.

FIG. 1 is a block diagram for explaining a diagnosis device using saliva according to an exemplary embodiment of the present invention, and FIG. 2 is a view for explaining an example of the diagnosis device illustrated in FIG. 1.

Referring to FIGS. 1 and 2, a diagnosis device 100 using saliva (hereinafter, referred to as a 'diagnosis device') according to the present invention is connected to a user terminal 200 via a communication network 300.

The diagnosis device 100 diagnoses a disease by using an electrochemical method using saliva instead of blood. In this case, the diagnosis device 100 may utilize (measure) saliva for each particular purpose (disease) by allowing a detection unit suitable for a particular purpose (disease) to react with saliva. Further, the diagnosis device 100, which includes: (i) an electronic device; and (ii) a detection unit 160 (strip electrode unit), converts diagnosis data into a digital signal and provides the digital signal to the user terminal 200 via the communication network 300.

The user terminal 200 is connected to the diagnosis device 100 via the communication network 300 and may transmit and receive various types of data to/from the diagnosis device 100.

That is, the user terminal 300 may convert the digital signal, which is provided from the diagnosis device 100 via the communication network 300, into concentration of a disease factor based on a predetermined calibration curve. Here, the disease factor is a particular factor capable of diagnosing a disease and refers to antigens, glucose, and the like. For example, in a case in which the disease factor is glucose, the calibration curve includes an electric current value in accordance with concentration of glucose, and the calibration curve may be acquired in advance through preceding experiments and the like. Further, the user terminal 300 may display the converted concentration of the disease factor.

Therefore, in a case in which the diagnosis device according to the present invention diagnoses diabetes, concentration of glucose related to diabetes is determined as numerical values in advance, and the diagnosis device may diagnose diabetes by using the numerical value and the diagnosis result, that is, quantified concentration of glucose.

Here, the user terminal 200 may be a terminal, which is equipped with a memory means and a microprocessor and has a calculation ability, such as a desktop computer, a notebook computer, a workstation, a palmtop computer, an ultra-mobile personal computer (UMPC), a tablet PC, a personal digital assistant (PDA), a web pad, a smartphone, and a mobile phone.

The communication network 300 may include a telephone network as well as a data communication network including a local area network (LAN), a metropolitan area network (MAN), a wide area network (WAN), and the Internet, and any communication method may be used regardless of a wired communication method and a wireless communication method.

Then, the diagnosis device according to the exemplary embodiment of the present invention will be described in more detail with reference to FIG. 3.

Figure 3:
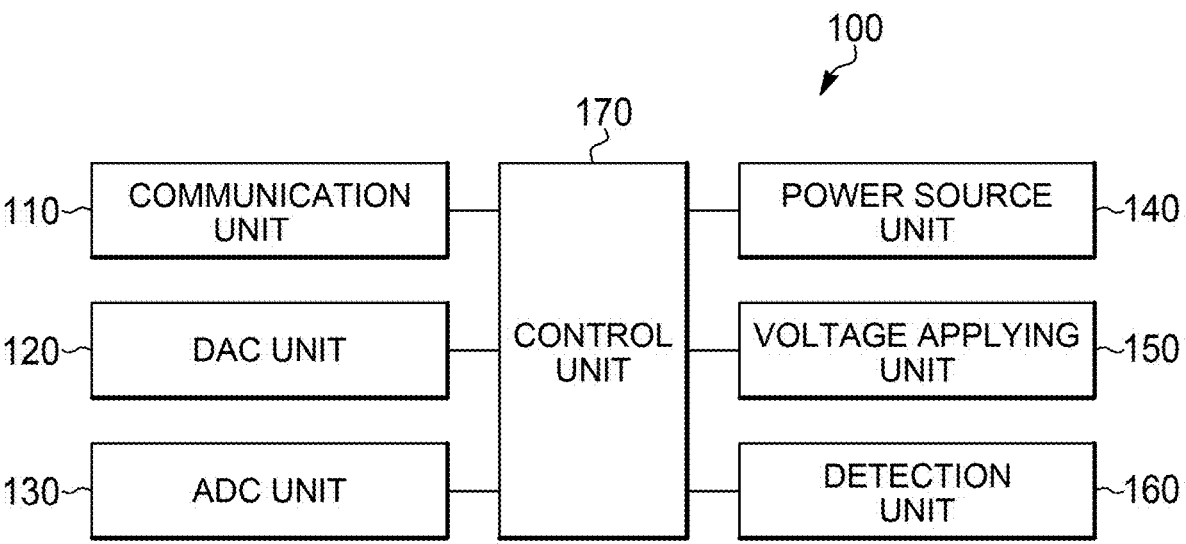
FIG. 3 is a block diagram illustrating in more detail a configuration of the diagnosis device illustrated in FIG. 1.

FIG. 3 is a block diagram illustrating in more detail a configuration of the diagnosis device illustrated in FIG. 1.

Referring to FIG. 3, the diagnosis device 100 may include a communication unit 110, a DAC unit 120, an ADC unit 130, a power source unit 140, a voltage applying unit 150, a detection unit 160, and a control unit 170.

The communication unit 110 has a wired communication module (not illustrated) or a wireless communication module (not illustrated) and serves to transmit and receive corresponding data for wired or wireless communication of the diagnosis device 100. For example, the communication unit 110 may transmit data, which are received from other constituent elements of the diagnosis device 100, to the user terminal 200 via the communication network 300.

The DAC unit 120 converts a digital signal into an analog signal under control of the control unit 170.

The ADC unit 130 converts an analog signal into a digital signal under control of the control unit 170.

The power source unit 140 includes a battery (not illustrated) and supplies electric power required to operate the respective constituent elements of the diagnosis device 100. Here, the battery may be an integral battery fixed to the diagnosis device 100 or a separable battery attachable to or detachable from the diagnosis device 100. Of course, the power source unit 140 may be supplied with electric power from an external power source (not illustrated).

The voltage applying unit 150 applies a predetermined voltage to the detection unit 160 under control of the control unit 170. Further, the voltage applying unit 150 measures electric current generated by the detection unit 160 and provides the electric current to the control unit 170.

The detection unit 160 is detachably coupled to the diagnosis device 100 and diagnoses a disease by using saliva. That is, the detection unit 160 induces an electrochemical reaction (that is, oxidation-reduction reaction) of a disease factor in sampled saliva by the voltage applied by the voltage applying unit 150.

Further, the detection unit 160 provides diagnosis data to the control unit 170. That is, the detection unit 160 provides the control unit 170, via the voltage applying unit 150, with the electric current generated by the electrochemical reaction of the disease factor.

The control unit 170 controls overall operations of the respective constituent elements of the diagnosis device 100.

In particular, the control unit 170 controls the voltage applying unit 150 to apply voltage to the detection unit 160. Further, the control unit 170 converts the diagnosis data, which are provided through the detection unit 160, into a digital signal by using the ADC unit 130. That is, the control unit 170 measures electric current, which is generated by the detection unit 160 by the electrochemical reaction of the disease factor, by using the voltage applying unit 150, and the control unit 170 may convert the measurement result into the digital signal.

In addition, the control unit 170 provides the user terminal 200 with the digital signal via the communication unit 110. Then, the user terminal 300 converts the digital signal, which is provided from the diagnosis device 100, into concentration of the disease factor based on a predetermined calibration curve.

Then, the detection unit according to the exemplary embodiment of the present invention will be described in more detail with reference to FIG. 4.

Figure 4:
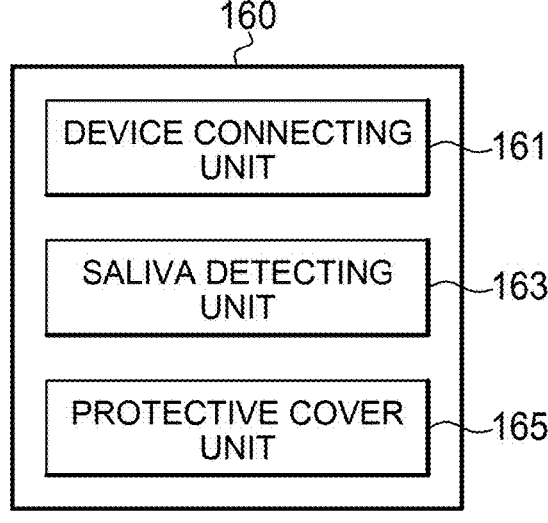
FIG. 4 is a block diagram illustrating in more detail a configuration of a detection unit illustrated in FIG. 3.

FIG. 4 is a block diagram illustrating in more detail a configuration of the detection unit illustrated in FIG. 3.

Referring to FIG. 4, the detection unit 160 may include a device connecting unit 161, a saliva detecting unit 163, and a protective cover unit 165.

The device connecting unit 161 is supplied with voltage from the diagnosis device 100. Further, the device connecting unit 161 provides the diagnosis device 100 with electric current generated by the electrochemical reaction of the disease factor in the saliva.

The saliva detecting unit 163 induces the electrochemical reaction of the disease factor in the saliva by the voltage applied from the diagnosis device 100 via the device connecting unit 161. Further, the saliva detecting unit 163 provides the device connecting unit 161 with the electric current generated by the electrochemical reaction of the disease factor. Here, saliva of a patient may be sampled as the patient spits out the saliva to the saliva detecting unit 163 or the saliva detecting unit 163 is brought into contact with a diseased part in an oral cavity of the patient. That is, the saliva detecting unit 163 may serve as a reactor which mixes the saliva sample of the patient and performs the electrochemical reaction.

The protective cover unit 165 is a housing for protecting the device connecting unit 161 and the saliva detecting unit 163 from outside substances or stimulation.

Then, an example of the detection unit according to the exemplary embodiment of the present invention will be described with reference to FIGS. 5 to 10.

Figure 7:
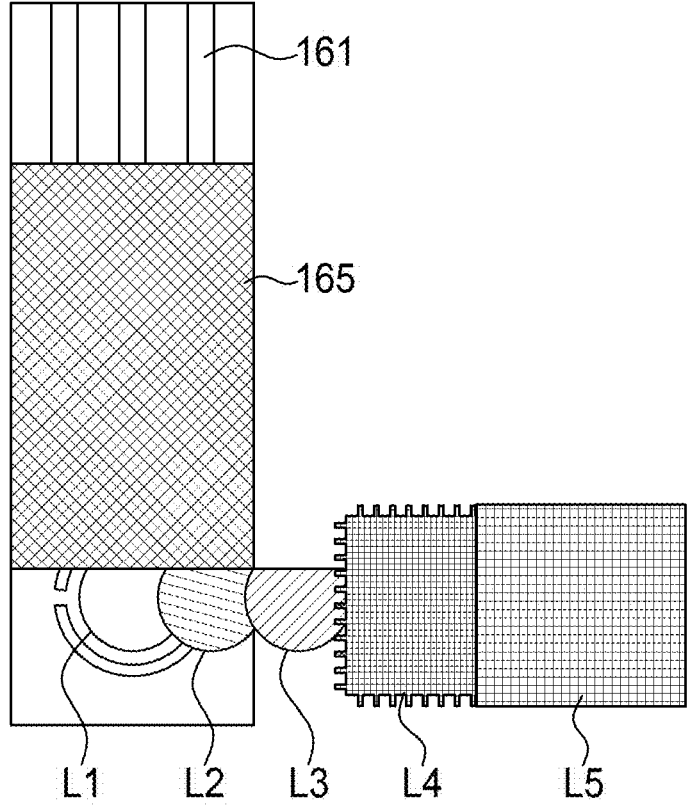
FIG. 7 is a view illustrating in more detail a configuration of a saliva detecting unit illustrated in FIG. 5.
Figure 8A:
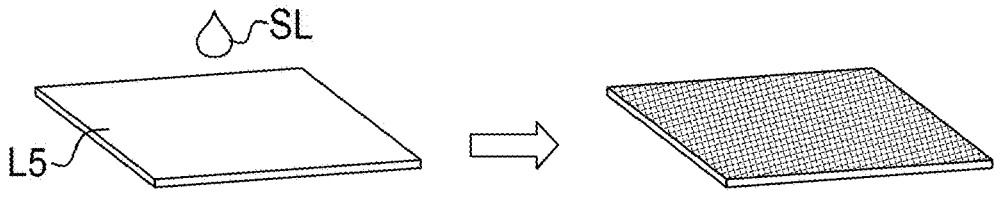
FIG. 8 is a view for explaining an example of individual processes of diagnosing a disease according to the exemplary embodiment of the present invention.
Figure 8B:
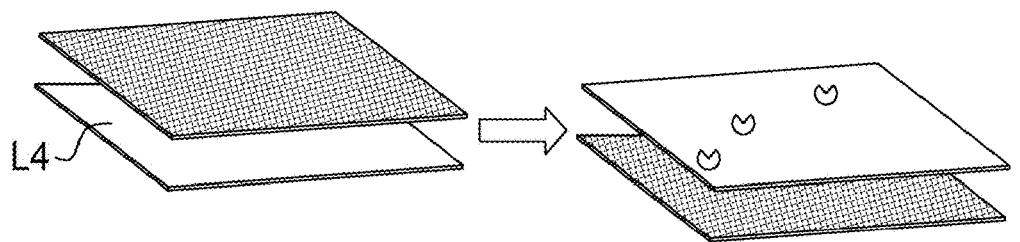
Figure 8C:
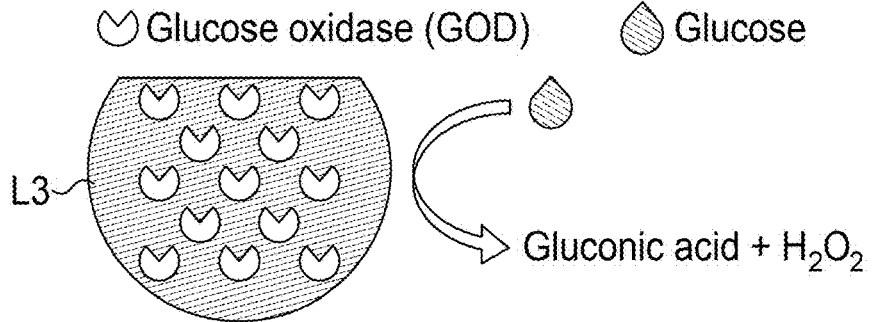
Figure 8D:
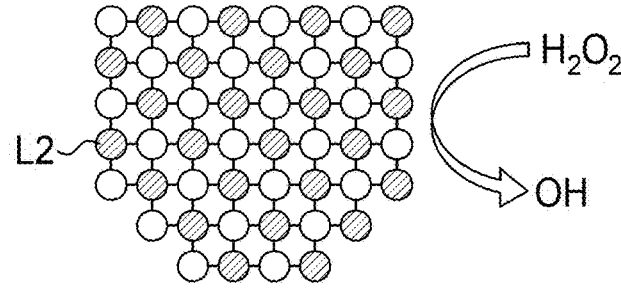
Figure 9:
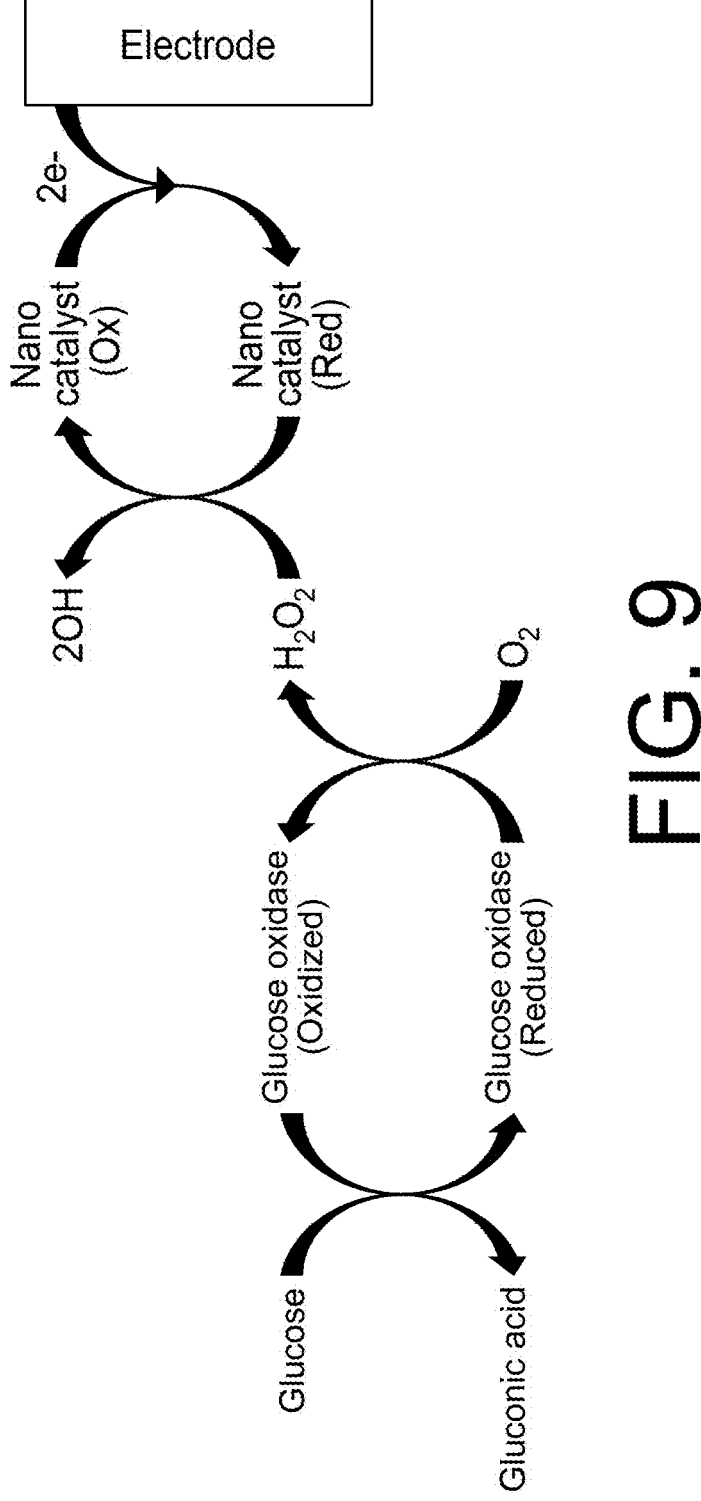
FIG. 9 is a view for explaining an example of an entire process of diagnosing a disease according to the exemplary embodiment of the present invention.
Figure 10A:
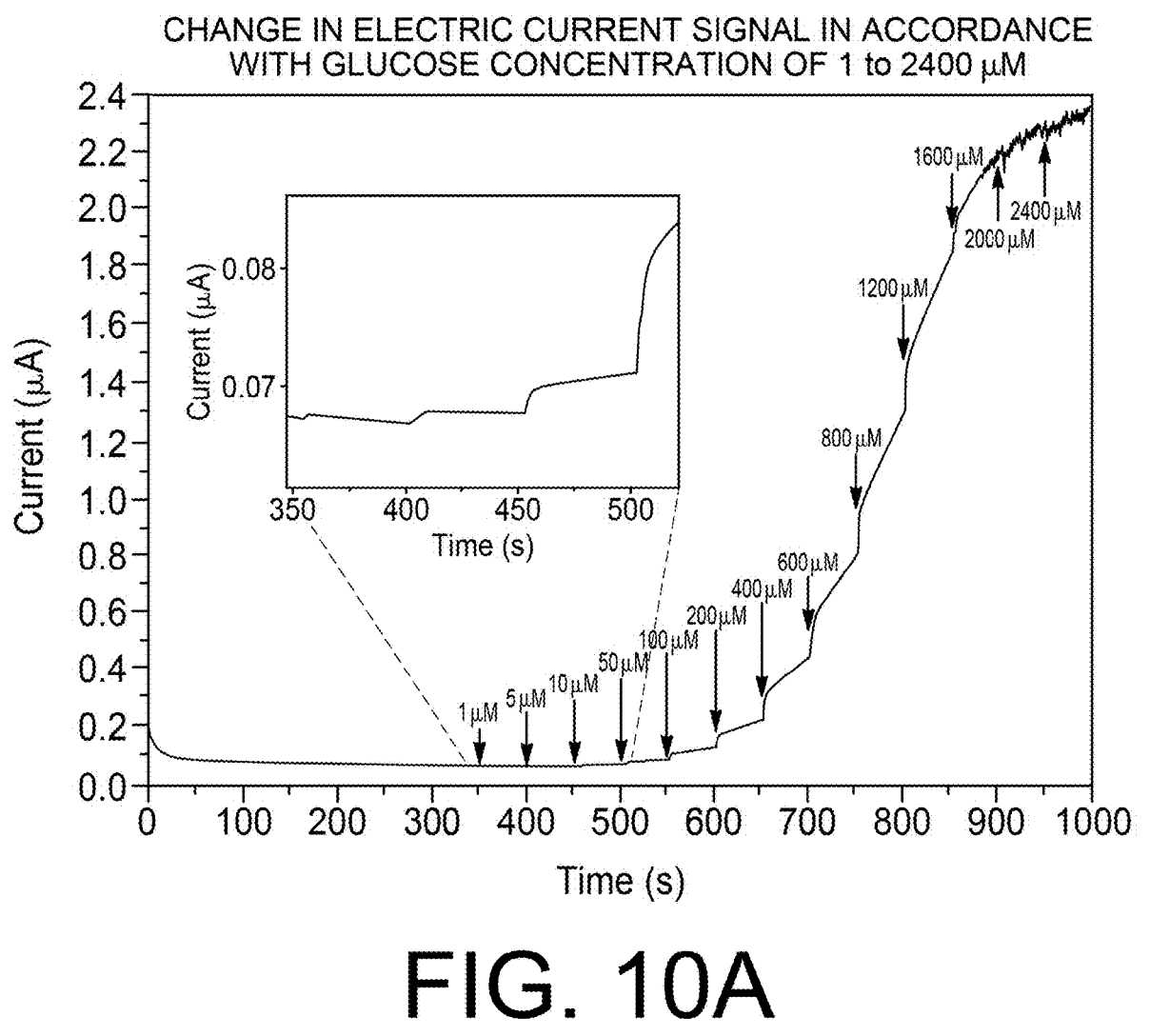
Figure 10B:
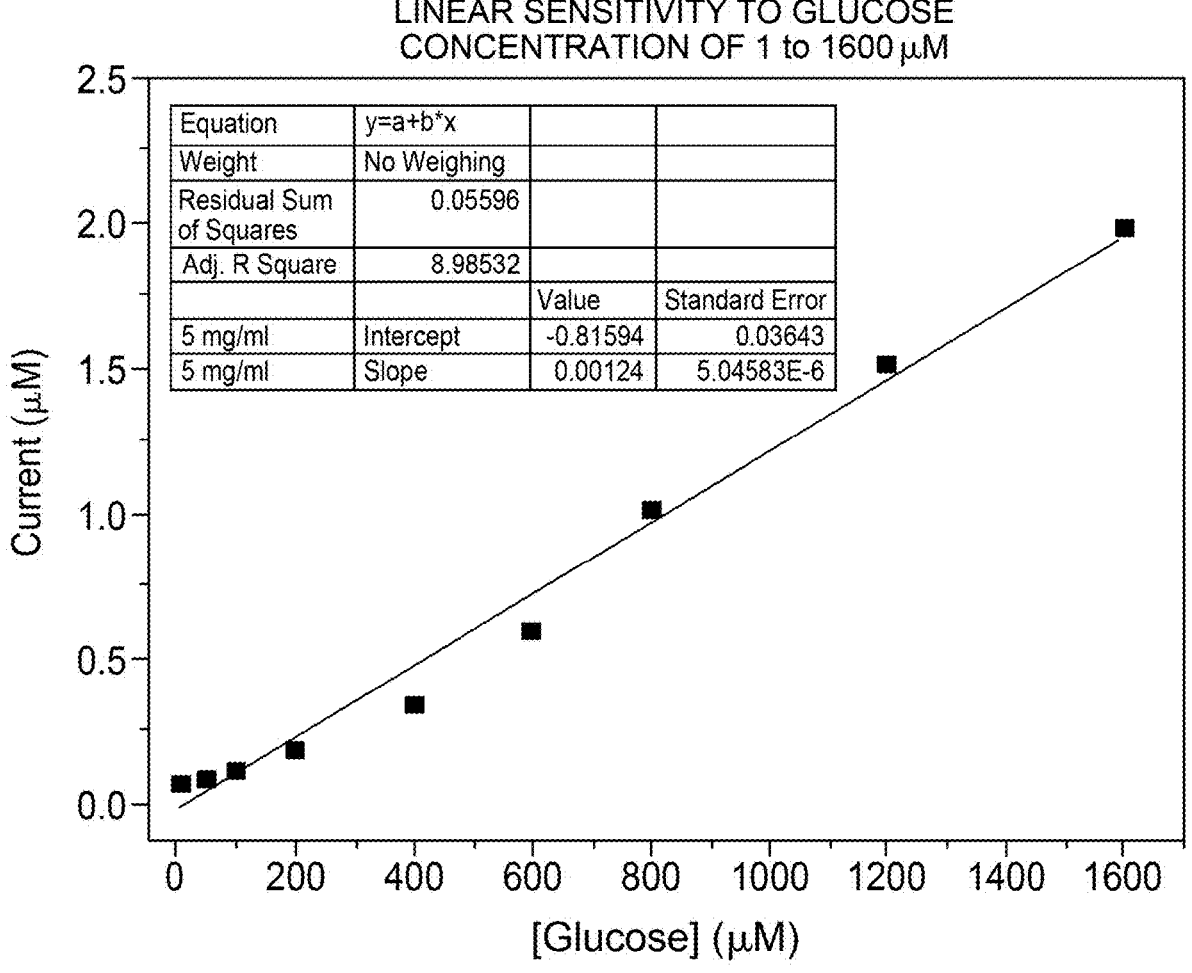
FIG. 10 is a graph for explaining an example of a disease diagnosis result according to the exemplary embodiment of the present invention.

FIG. 5A is a view for explaining an example of the detection unit illustrated in FIG. 3, and FIG. 5B is a cross-sectional view taken along line A-A' illustrated in FIG. 5A, FIG. 6 is a view for explaining a state in which a protective cover unit is separated from the detection unit illustrated in FIG. 5, FIG. 7 is a view illustrating in more detail a configuration of a saliva detecting unit illustrated in FIG. 5, FIG. 8 is a view for explaining an example of individual processes of diagnosing a disease according to the exemplary embodiment of the present invention, FIG. 9 is a view for explaining an example of an entire process of diagnosing a disease according to the exemplary embodiment of the present invention, and FIG. 10 is a graph for explaining an example of a disease diagnosis result according to the exemplary embodiment of the present invention.

Referring to FIGS. 5 to 10, the saliva detecting unit 163 according to the present invention may include multiple layers L1 to L5.

The fifth layer L5 is positioned on the fourth layer LA and formed by a composite fiber membrane. That is, as illustrated in FIG. 8A, when saliva SL comes into contact with the fifth layer L5 formed by the composite fiber membrane, the fifth layer L5 disperses the saliva to the entire composite fiber membrane.

The fourth layer LA is positioned on the third layer L3 and configured as a filter for separating predetermined materials. That is, as illustrated in FIG. 8B, the fourth layer LA separates the predetermined materials among the multiple materials included in the saliva. For example, many materials such as protein, amylase, and urea are included in the saliva in addition to glucose, and in the case in which the disease factor is glucose, the fourth layer L4 may separate a material that hinders the detection of glucose. Of course, in a case in which the disease factor is not glucose but another factor, the fourth layer L4 may separate a material that hinders the detection of the factor.

The third layer L3 is positioned on the second layer L2 and may include an enzyme that detects the disease factor in the saliva. That is, as illustrated in FIG. 8C, in the case in which the disease factor is glucose, the third layer L3 decomposes the glucose into hydrogen peroxide and gluconic acid. In addition, in a case in which the disease factor is not glucose but another factor, the third layer L3 may include an enzyme that may detect the factor in the saliva. Therefore, the present invention may constitute the saliva detecting unit 163 by using the third layer L3 that may detect a disease factor related to a disease to be measured. As described above, the detection unit may be selected and used for measurement for each particular purpose (disease), and as a result, the present invention may provide an economic advantage in that various disease factors may be selectively detected in addition to glucose.

The second layer L2 is attached to the first layer L1 and induces an electrochemical reaction of a disease factor in saliva. That is, as illustrated in FIG. 8D, in the case in which the disease factor is glucose, the second layer L2 reduces hydrogen peroxide produced when the third layer L3 decomposes glucose, the second layer L2 itself is oxidized, and in this process, electric current is generated while electrons are transmitted and received.

In this case, the second layer L2 may have a nanostructure in the form of a porous metal-organic solid structure. The nanostructure is a nontoxic catalyst having no biological risk, the nanostructure reduces a product of a metabolic reaction of glucose by using an electrochemical method, and the nanostructure itself is oxidized again at the electrode, thereby generating an electric current signal.

Further, the nanostructure has a chemical composition, $M_a(II)M'_b(III)(CN)_6$, and M and M' may be metal elements. For example, a solid structure, which is made of a coordinate compound including metal positive ions, $M^{2+}$ and $M^{3+}$, and a negative ion, that is, a cyanide ion, $CN^-$, promotes a quick reduction reaction of hydrogen peroxide, which is a metabolite of an enzyme, because of electrochemical catalytic characteristics of the center metal positive ion. M and M', which are metal elements, may be Fe, Zn, K, Mg, Al, Cu, Co, Ni, Cr, Mn, Rb, or the like, and as an example, the nanostructure may be a structure in the form of Prussian blue, $Fe_4^{III}[Fe^{II}(CN)_6]_3$ based on $Fe^{2+}$ and $Fe^{3+}$. With this nanostructure, it is possible to constitute the saliva detecting unit 163 having high sensitivity. For example, as illustrated in FIG. 10, by using the nanostructure, with respect to the detection amount, the present invention may acquire detection sensitivity (detection limit=10 to 1 µM) of 100 to 1,000 times sensitivity of the existing blood glucose sensor that adopts a blood drawing method.

The first layer L1 is configured as an electrode connected to the device connecting unit 161. That is, the first layer L1 provides the device connecting unit 161 with the electric current generated by the second layer L2. Meanwhile, the first layer L1 is illustrated, in the drawing, as having three electrodes including a reference electrode EN1, a working electrode EN2, and an auxiliary electrode EN3, but the first layer L1 is not limited thereto, and the first layer L may have two electrodes in accordance with an exemplary embodiment.

Meanwhile, the saliva detecting unit 163 is illustrated, in the drawing, as having the first to fifth layers L1 to L5, but the saliva detecting unit 163 is not limited thereto, and the saliva detecting unit 163 may further include a filtration membrane or a thin membrane in accordance with an exemplary embodiment. For example, the saliva detecting unit 163 may further include a filtration membrane that may sense only a particular disease factor from various interfering materials in saliva. In addition, the saliva detecting unit 163 may further include a thin membrane which serves as protein or a DNA material and an electrolyte that sense a selective electrochemical signal related only to a disease factor.

Then, a diagnosis method using the diagnosis device using saliva according to the exemplary embodiment of the present invention will be described with reference to FIG. 11.

Figure 11:
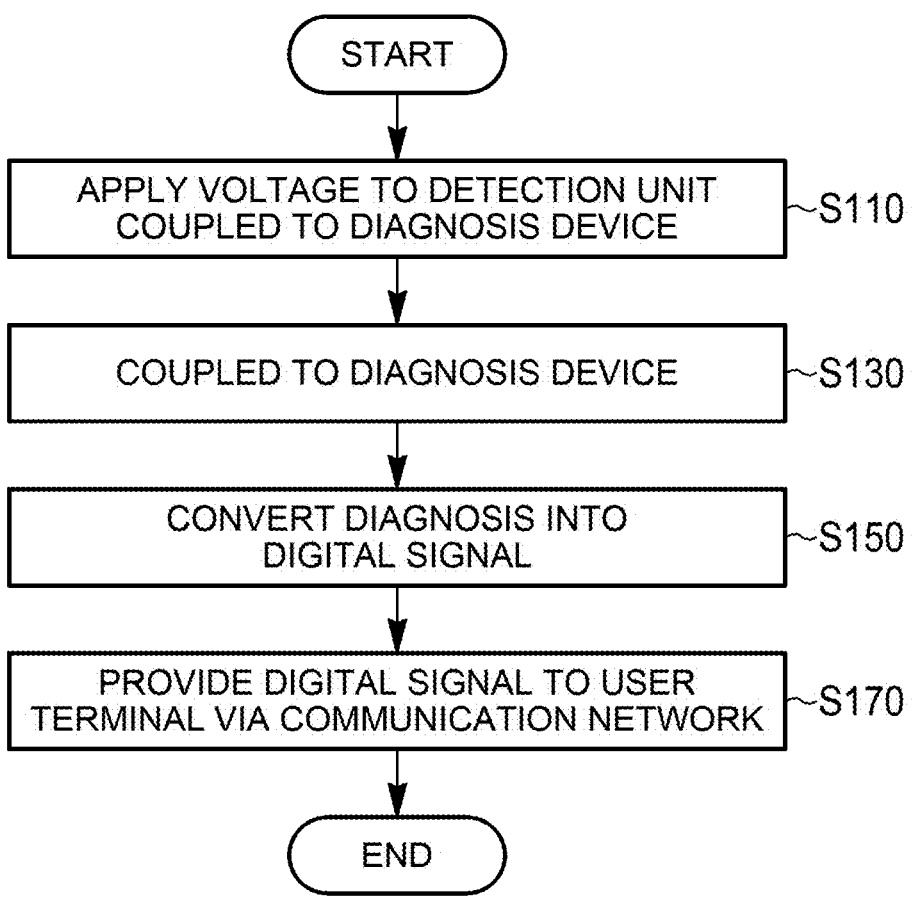
FIG. 11 is a flowchart for explaining a diagnosis method using the diagnosis device using saliva according to the exemplary embodiment of the present invention.

FIG. 11 is a flowchart for explaining the diagnosis method using the diagnosis device using saliva according to the exemplary embodiment of the present invention.

Referring to FIG. 11, the diagnosis device 100 applies a predetermined voltage to the detection unit 160 coupled to the diagnosis device 100 (S110).

Then, the diagnosis device 100 diagnoses a disease by using saliva (S130). That is, the detection unit 160 induces an electrochemical reaction of a disease factor in sampled saliva by the applied voltage. Further, the detection unit 160 provides the diagnosis device 100 with electric current generated by the electrochemical reaction of the disease factor.

Further, the diagnosis device 100 converts diagnosis data (that is, a result of measuring the electric current generated by the detection unit 160) into a digital signal (S150).

Then, the diagnosis device 100 provides the digital signal to the user terminal 200 via the communication network 300 (S170). Then, the user terminal 200 converts the digital signal, which is provided from the diagnosis device 100, into concentration of the disease factor based on a predetermined calibration curve.

The present invention may also be implemented as computer-readable codes written on a computer-readable recording medium. The computer-readable recording medium includes all types of recording devices on which data may be recorded in a computer-readable manner. For example, the computer-readable recording medium includes a ROM, a RAM, a CD-ROM, a magnetic tape, a floppy disk, an optical data storage device, and a carrier wave (for example, transmission via the Internet). In addition, the computer-readable recording medium may be distributed over computer devices connected one another via wired and wireless communication networks, such that computer-readable codes may be stored and executed in the computer-readable recording medium in a decentralized manner.

While the exemplary embodiments of the present invention have been described in detail as described above, the present invention is not limited to the aforementioned particular exemplary embodiments, and the present invention may be variously modified by those skilled in the art to which the present invention pertains without departing from the subject matters of the present invention claimed in the appended claims, and the modifications belong to the scope disclosed in the appended claims.

The invention claimed is:

1. A non-invasive diagnosis system for analyzing a concentration of glucose in a sample of saliva, the non-invasive diagnosis system comprising:

an electronic device; and a detection unit which is detachably coupled to the electronic device and configured to induce an electrochemical reaction in the sample of saliva in response to a voltage applied by the electronic device, and provide an electric current generated by the electrochemical reaction to the electronic device, wherein the electric current is indicative of the concentration of glucose in the sample of saliva, wherein the electronic device applies the voltage to the detection unit, receives the electric current from the detection unit, and converts the electric current into a digital signal, wherein the detection unit includes a non-implantable strip which is configured to receive the sample of saliva, the strip including:

a first layer which comprises two or more electrodes;

a second layer which has a nanostructure in the form of a porous metal organic solid structure and is attached as a catalyst on the first layer to induce the electrochemical reaction of the glucose in the sample of saliva;

a third layer which is positioned on the second layer and comprises an enzyme which is used for detecting glucose in the sample of saliva;

a fourth layer which is positioned on and directly overlaying the third layer and comprises a filter for separating any one of materials selected from protein, amylase, and urea that hinder a detection of glucose; and a fifth layer which is positioned on the fourth layer and comprises a composite fiber membrane, wherein the fifth layer is configured to disperse the saliva throughout the composite fiber membrane.

2. The non-invasive diagnosis system according to claim 1, wherein the nanostructure has a chemical composition of $M_a(II)M'_b(III)(CN)_6$, and wherein each of M and M' is any one of metal elements selected from the group consisting of: Fe, Zn, K, Mg, Al, Cu, Co, Ni, Cr, Mn and Rb.

3. A non-invasive diagnosis method using a non-invasive diagnosis system including an electronic device and a detection unit for analyzing a concentration of glucose in a sample of saliva, the non-invasive diagnosis method comprising:

applying, by the electronic device, a voltage to the detection unit, which is detachably coupled to the electronic device;

inducing, by the detection unit, an electrochemical reaction of glucose in the sample of saliva in response to the voltage applied to the detection unit, and providing, by the detection unit, an electric current generated by the electrochemical reaction; and receiving, by the electronic device, the electric current from the detection unit, and converting, by the electronic device, the electric current into a digital signal, wherein the detection unit includes a non-implantable strip which is configured to receive the sample of saliva, the strip including:

a first layer which comprises two or more electrodes;

a second layer which has a nanostructure in the form of a porous metal organic solid structure and is attached as a catalyst on the first layer to induce the electrochemical reaction of glucose in the sample of saliva;

a third layer which is positioned on the second layer and comprises an enzyme which is used for detecting glucose in the sample of saliva;

a fourth layer which is positioned on and directly overlaying the third layer and comprises a filter for separating any one of materials selected from protein, amylase, and urea that hinder a detection of glucose; and a fifth layer which is positioned on the fourth layer and comprises a composite fiber membrane, wherein the fifth layer is configured to disperse the saliva throughout the composite fiber membrane.

4. The non-invasive diagnosis method according to claim 3, wherein the nanostructure has a chemical composition of $M_a(II)M'_b(III)(CN)_6$, and wherein each of M and M' is any one of metal elements selected from the group consisting of: Fe, Zn, K, Mg, Al, Cu, Co, Ni, Cr, Mn and Rb.

5. The non-invasive diagnosis system according to claim 1, wherein the electronic device includes a communication unit, and wherein the electronic device provides the digital signal to a separate user terminal through the communication unit.

6. The non-invasive diagnosis system according to claim 1, wherein the detection unit is a planar multi-tiered unit comprising at least five layers arranged in tiers.

7. The non-invasive diagnosis method according to claim 3, the non-invasive diagnosis method further comprising:

providing, by the electronic device, the digital signal to a separate user terminal via a communication network, wherein the digital signal is converted into the concentration of glucose by the separate user terminal based on a predetermined calibration curve.

8. The non-invasive diagnosis method according to claim 3, wherein the detection unit is a planar multi-tiered unit comprising at least five layers arranged in tiers.

9. A non-invasive detection unit for detecting a concentration of glucose in a sample of saliva, the non-invasive detection unit comprising a non-implantable strip which is configured to receive the sample of saliva, the strip including:

a first layer which comprises two or more electrodes;

a second layer which has a nanostructure in the form of a porous metal organic solid structure and is attached as a catalyst on the first layer to induce the electrochemical reaction of glucose in the sample of saliva;

a third layer which is positioned on the second layer and comprises an enzyme which is used for detecting glucose in the sample of saliva;

a fourth layer which is positioned on and directly overlaying the third layer and comprises a filter for separating any one of materials selected from protein, amylase, and urea that hinder a detection of glucose; and a fifth layer which is positioned on the fourth layer and comprises a composite fiber membrane, wherein the fifth layer is configured to disperse the saliva throughout the composite fiber membrane, wherein the non-invasive detection unit is detachably coupled to an electronic device and induces an electrochemical reaction of glucose in the sample of saliva in response to a voltage applied by the electronic device, and provides an electric current generated by the electrochemical reaction of glucose to the electronic device, and wherein the electronic device applies the voltage to the non-invasive, non-implantable detection unit, receives the electric current from the non-invasive detection unit, and converts the electric current into a digital signal.

10. The non-invasive detection unit according to claim 9, wherein the electronic device includes a communication unit, and wherein the electronic device provides the digital signal to a separate user terminal through the communication unit.

11. The non-invasive detection unit according to claim 9, wherein the non-invasive detection unit is a planar multi-tiered unit comprising at least five layers arranged in tiers.

12. The non-invasive detection unit according to claim 9, wherein the nanostructure has a chemical composition of $M_a(II)M'_b(III)(CN)_6$, and wherein each of M and M' is any one of metal elements selected from the group consisting of: Fe, Zn, K, Mg, Al, Cu, Co, Ni, Cr, Mn and Rb.

13. An electronic device being a part of a non-invasive diagnosis system including the electronic device and a non-invasive detection unit for analyzing a concentration of glucose in a sample of saliva, the electronic device comprising:

a control unit, wherein the non-invasive detection unit is detachably coupled to the electronic device, induces an electrochemical reaction of glucose in the sample of saliva in response to a voltage applied by the control unit, and provides an electric current generated by the electrochemical reaction, wherein the control unit applies the voltage to the non-invasive detection unit, receives the electric current from the non-invasive detection unit, and converts the electric current into a digital signal, wherein the non-invasive detection unit includes a non-implantable strip which is configured to receive the sample of saliva, the strip including:

a first layer which comprises a working electrode, a reference electrode, and an auxiliary electrode;

a second layer which has a nanostructure in the form of a porous metal organic solid structure and is attached as a catalyst on the first layer to induce the electrochemical reaction of glucose in the sample of saliva;

a third layer which is positioned on the second layer and comprises an enzyme which is used for detecting glucose in the sample of saliva;

a fourth layer which is positioned on and directly overlaying the third layer and comprises a filter for separating any one of materials selected from protein, amylase, and urea that hinder a detection of glucose; and a fifth layer which is positioned on the fourth layer and comprises a composite fiber membrane, wherein the fifth layer is configured to disperse the saliva throughout the composite fiber membrane.

14. The electronic device according to claim 13, the electronic device further comprising:

a communication unit, wherein the control unit provides the digital signal to a separate user terminal through the communication unit.

15. The electronic device according to claim 13, wherein the non-invasive detection unit is a planar multi-tiered unit comprising at least five layers arranged in tiers.

16. The electronic device according to claim 13, wherein the nanostructure has a chemical composition of $M_a(II)M'_b(III)(CN)_6$, and wherein each of M and M' is any one of metal elements selected from the group consisting of: Fe, Zn, K, Mg, Al, Cu, Co, Ni, Cr, Mn and Rb.

17. The non-invasive diagnosis system of claim 1, wherein the filter is configured to separate amylase or urea.

18. The non-invasive diagnosis method of claim 3, wherein the filter is configured to separate amylase or urea.

19. The non-invasive detection unit of claim 9, wherein the filter is configured to separate amylase or urea.

20. The electronic device of claim 13, wherein the filter is configured to separate amylase or urea.

21. The non-invasive diagnosis system of claim 17, wherein the filter is configured to separate urea.

22. The non-invasive diagnosis system of claim 1, wherein the fifth layer is configured to receive the sample of saliva from saliva spit onto the detection unit by a user.

23. The non-invasive diagnosis method of claim 17, wherein the filter is configured to separate urea.

24. The non-invasive diagnosis method of claim 18, wherein the fifth layer is configured to receive the sample of saliva from saliva spit onto the detection unit by a user.

25. The non-invasive detection unit of claim 19, wherein the filter is configured to separate urea.

26. The non-invasive detection unit of claim 9, wherein the fifth layer is configured to receive the sample of saliva from saliva spit onto the detection unit by a user.

27. The electronic device of claim 20, wherein the filter is configured to separate urea.

28. The electronic device of claim 13, wherein the fifth layer is configured to receive the sample of saliva from saliva spit onto the detection unit by a user.

* * * * *